US 8,142,427 B2

(12) United States Patent
Pearson et al.

(10) Patent No.: US 8,142,427 B2
(45) Date of Patent: Mar. 27, 2012

(54) INVASIVE ABLATION PROBE WITH NON-CORING DISTAL TIP

(75) Inventors: Christopher Pearson, Grafton, MA (US); Robert Garabedian, Tyngsboro, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1394 days.

(21) Appl. No.: 10/831,244

(22) Filed: Apr. 23, 2004

(65) Prior Publication Data
US 2005/0240174 A1 Oct. 27, 2005

(51) Int. Cl.
*A61B 18/18* (2006.01)
(52) U.S. Cl. .......................................... 606/41
(58) Field of Classification Search ............... 600/374, 600/471, 474; 606/41
See application file for complete search history.

(56) References Cited

U.S. PATENT DOCUMENTS

| | | | | |
|---|---|---|---|---|
| 396,754 | A | * | 1/1889 | Mayfield ........................ 604/249 |
| 4,699,147 | A | * | 10/1987 | Chilson et al. ................. 600/374 |
| 5,166,990 | A | * | 11/1992 | Riccitelli et al. ................ 385/12 |
| 5,281,218 | A | | 1/1994 | Imran |
| 5,293,869 | A | * | 3/1994 | Edwards et al. ............... 600/375 |
| 5,827,276 | A | | 10/1998 | LeVeen et al. |
| 5,855,576 | A | * | 1/1999 | LeVeen et al. ................... 606/41 |
| 5,951,547 | A | * | 9/1999 | Gough et al. .................... 606/41 |
| 6,425,887 | B1 | | 7/2002 | McGuckin et al. |
| 6,500,175 | B1 | | 12/2002 | Gough et al. |
| 6,575,967 | B1 | | 6/2003 | Leveen et al. |
| 6,622,731 | B2 | | 9/2003 | Daniel et al. |
| 6,890,307 | B2 | * | 5/2005 | Kokate et al. ................... 600/549 |
| 6,932,814 | B2 | * | 8/2005 | Wood ............................... 606/41 |
| 2002/0151867 | A1 | | 10/2002 | McGuckin, Jr. et al. |
| 2002/0198520 | A1 | * | 12/2002 | Coen et al. ....................... 606/41 |

FOREIGN PATENT DOCUMENTS
WO 96/10367 4/1996

OTHER PUBLICATIONS

PCT International Search Report for PCT/US2005/009082, Applicant: Boston Scientific Scimed, Inc., Forms PCT/ISA/210 and 220, dated Jul. 13, 2005 (7 pages).
PCT Written Opinion of the International Search Authority for PCT/US2005/009082, Applicant: Boston Scientific Scimed, Inc., Form PCT/ISA/237, dated Jul. 13, 2005 (5 pages).

* cited by examiner

*Primary Examiner* — Darwin Erezo
*Assistant Examiner* — Gregory Anderson
(74) *Attorney, Agent, or Firm* — Vista IP Law Group LLP

(57) ABSTRACT

An invasive medical device for delivery radio frequency energy to a target tissue region includes an elongate delivery cannula having a lumen in communication with a distal opening. A deployment member is positioned and longitudinally movable in the lumen. An array of electrode elements are secured to a distal end of the deployment member, the deployment member being movable from a delivery position, in which the electrode elements are positioned within the lumen, to a deployed position, in which the electrode elements extend distally out of the cannula distal opening. A sealing member formed from a biocompatible material sufficiently rigid to penetrate solid body tissue partially extends from, and substantially seals, the distal cannula opening when the deployment member is in the delivery position. By way of examples, the sealing member may be carried on a distal end of the deployment member, or on a separately movable deployment member, or frictionally fit in the cannula distal opening.

25 Claims, 7 Drawing Sheets

INVASIVE ABLATION PROBE WITH NON-CORING DISTAL TIP

FIELD OF INVENTION

The invention pertains generally to invasive medical devices and, more particularly, to invasive devices for locating and deploying electrode elements for delivery radio frequency energy to tissue regions in a body.

BACKGROUND

Invasive, needle-like devices for positioning an array of deployable electrode elements for applying radio frequency energy to heat a target tissue structure, e.g., a tumor, are well-known. By way of one example illustrated in FIGS. 1 and 2, a radio frequency (RF) ablation probe 20, and in particular, a LeVeen Needle™ electrode, manufactured and distributed by Boston Scientific Corporation, includes a tubular deployment cannula 22 having an internal axial lumen 24 (shown in FIG. 3), which terminates at a distal opening 40, and a sharpened, tissue-penetrating distal tip 26. The cannula 22 is provided with a handle 28 to allow a physician to more easily grasp the proximal end of the ablation probe 20 when inserting the distal end into solid tissue, e.g., through the abdominal wall and liver tissue of a patient.

An array of tissue piercing electrode elements in the form of tines 30 are secured about the circumference of a tubular deployment member 32 seated coaxially within the cannula lumen 24 (shown in FIG. 3). The electrode tines 30 are formed of a substantially flat wire, each having a tissue piercing tip 34 for easy tracking through solid tissue. The tines 30 are made of a shape-memory stainless steel, and are flexible to take on a substantially linear shape when constrained in the cannula lumen 24 (shown in FIG. 3), and a curved, everting shape when deployed outside of the cannula lumen 24 (shown in FIG. 2). An output of an RF generator (not shown) is electrically coupled to the deployment member 32, which, itself, is electrically coupled to the electrode tines 30, such that an RF signal applied from the generator output is transmitted to the electrode tines 30, and to tissue in which the electrode tines 30 are deployed.

A proximal plunger 38 is fixed to the deployment member 32, such that movement of the plunger 38 relative to the handle 28 provides for alternate deployment of the electrode tines 30 out of, or into, the cannula lumen 24. More particularly, as shown in FIG. 1, prior to insertion of the sharpened distal tip 26 of the cannula 22 into body tissue, the plunger 38 is pulled back (or otherwise initially placed) in a position most proximal to the handle 28, with the electrode tines 30 completely constrained by and carried within the cannula lumen 24. While grasping the handle 28, the physician inserts the cannula 22 into the body tissue until the cannula tip 26 is located at a target tissue region TR, for example a tumor, using ultrasound or some other imaging modality (not shown) for guidance in locating the cannula tip 26.

As shown in FIG. 2, once the cannula tip 26 is at the target tissue region TR, the plunger 38 is moved toward the handle 28, so that the electrode tines 30 are deployed into the tissue region TR, taking on an everting, i.e., umbrella or mushroom shaped, formation. A patient return electrode (not shown) is also coupled to the RF generator in order to complete an electrical circuit. The return electrode is relatively large and acts as an "infinite" ground, such that substantially all of the RF energy from the generator is delivered into the tissue immediately adjacent the electrode tines 30. This mode of operation is commonly referred to as monopolar operation.

More comprehensive details of the LeVeen Needle™ device, and similar RF tissue treatment devices and their operation are disclosed and described in U.S. Pat. No. 6,575,967, which is incorporated by reference herein for all it teaches and describes.

Notably, one disadvantage of the afore-described LeVeen Needle™ device is that the delivery cannula lumen necessarily has a relatively large inner diameter and open distal end, in order to carry and deploy the electrode tines in the internal body tissue. As a result, undesirable tissue coring can occur in the delivery path as the distal tip of the cannula is moved through the tissue to the target region. In addition to the injury caused to the tissue path, such coring can also result in a compacted tissue plug jammed into the distal opening of the cannula, which may interfere with proper deployment of the electrode tines.

The Co-Access™ electrode device, manufactured and distributed by Boston Scientific Corporation, overcomes this problem, as described in detail in above-incorporated U.S. Pat. No. 6,575,967, by providing a separate obtuator for accessing the target tissue region. Such obturator devices are well-known, and have a blunt tip delivery cannula with a lumen through which a solid, tissue piercing stylet is inserted. The delivery cannula, with the stylet in place, is used to access the desired tissue region. The stylet is then withdrawn, leaving the distal opening of the delivery cannula in a target tissue region. A second blunt-tipped cannula carrying the deployable electrode tines is then inserted through the lumen of the first cannula. Deployment of the electrode tines, and operation of the Co-Access™ device is otherwise the same as for the LeVeen Needle™ device described above. While the Co-Access™ device avoids unwanted tissue coring, it requires extra components and steps for locating and deploying the electrode tines into a target tissue region.

SUMMARY OF THE INVENTION

In accordance with the invention, an invasive medical device for the delivery of ablation energy (e.g., radio frequency (RF) energy) to body tissue is provided. The medical device comprises an elongate delivery cannula having a lumen in communication with a distal opening, a deployment member longitudinally movable in the lumen, and at least one ablation element (e.g., an array of tissue-piercing electrode tines) secured to a distal end of the deployment member. The deployment member is movable from a delivery position, in which the ablative element(s) is positioned within the lumen, to a deployed position, in which the ablative element(s) extends distally out of the cannula distal opening.

The medical device further comprises a sealing member at least partially extending from, and substantially sealing, the distal cannula opening when the deployment member is in the deliver position. In this manner, the ablative element(s) can be delivered to a targeted body tissue region, without causing unwanted coring of tissue in the insertion path.

The sealing member can take various forms. For example, the sealing member can have a tissue-penetrating distal tip, such as, a conically- or pyramidally-shaped distal tip. In this case, the cannula may have a blunted distal tip, since the tissue-penetrating functionality of the medical device will be provided by the sealing member. Or the sealing member can have a blunted distal tip, in which case, the cannula should have a tissue-penetrating distal tip.

The sealing member may have additional functionality besides preventing tissue coring. For example, the sealing member may comprises an electrode and/or temperature sensor. Or the sealing member may provide fluid delivery, in which case, it may have an opening in fluid communication with a channel extending through the deployment member associated with the deployment member.

The sealing member may be affixed in the medical device in a variety of manners. For example, the sealing member may be carried by the distal end of the deployment member distal to the ablative element(s), such that movement of the deployment member to the deployed position moves the sealing member distal to the distal cannula opening, allowing the ablative element(s) to be extended therefrom without obstruction from the sealing member. Or the sealing member may be carried on a distal end of another deployment member longitudinally movable in the lumen. The other deployment member may be positioned coaxially with the first deployment member, e.g., positioned telescopically with the deployment member. This arrangement will allow the deployment members to be movable independent of one another, thereby allowing deployment of the ablative element(s) and sealing member to be accomplished independently of one another. Or the sealing member may be frictionally fit in the cannula distal opening, such that movement of the deployment member from the delivery position to the deployed position detaches the sealing member from the cannula. In this case, the sealing member is preferably composed of a bioabsorbable material, so that it need not be retrieved from the patient's body after it is detached from the cannula.

Other and further aspects and features of the invention will be evident from reading the following detailed description of the illustrated embodiments, which are intended to illustrate, not limit, the invention.

BRIEF DESCRIPTION OF DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 4:
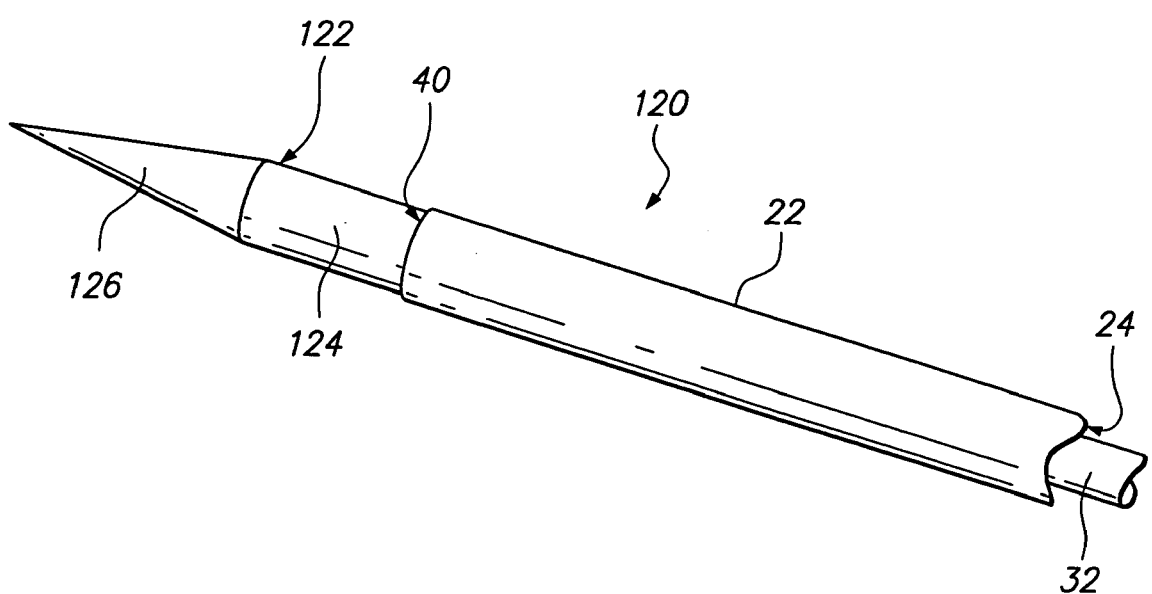
FIG. 4 is a partially cut-away perspective view of the distal end of an RF ablation probe constructed in accordance with a preferred embodiment of the invention.
Figure 5:
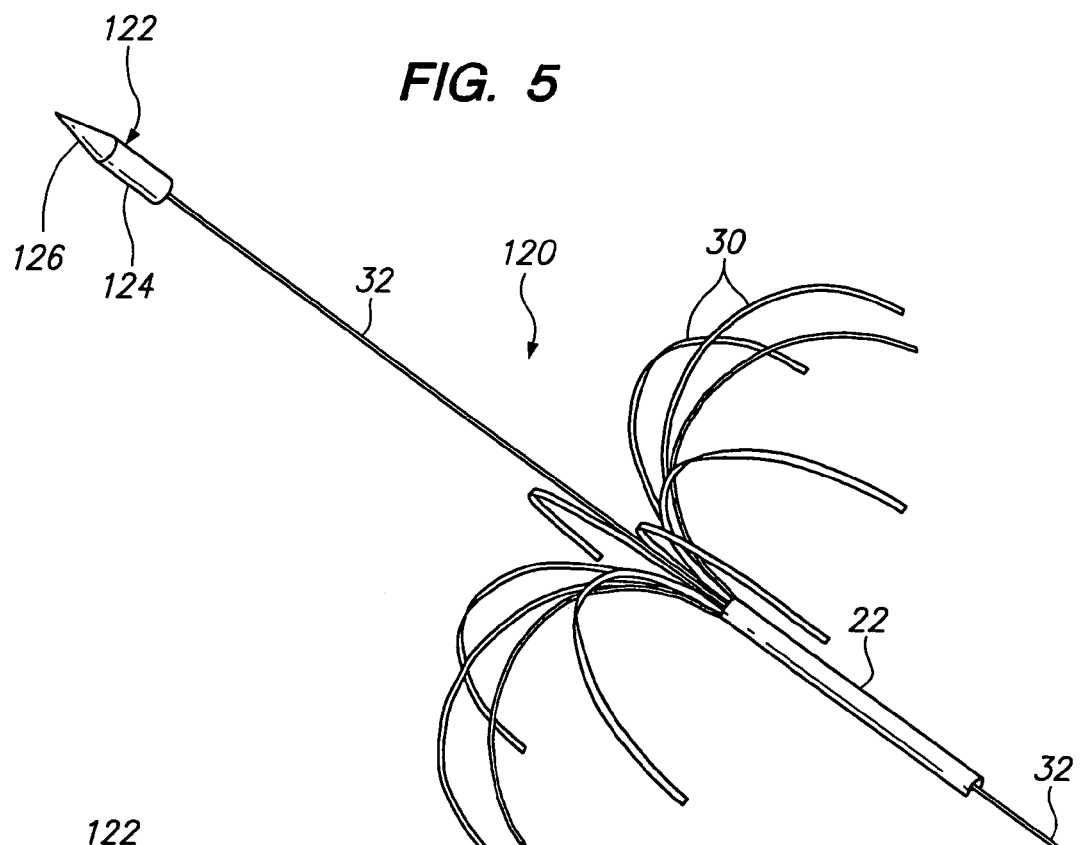
FIG. 5 is a partially cut-away perspective view of the distal end of the RF ablation probe of FIG. 4, particularly showing deployment of the sealing member and electrode tine array.
Figure 6:
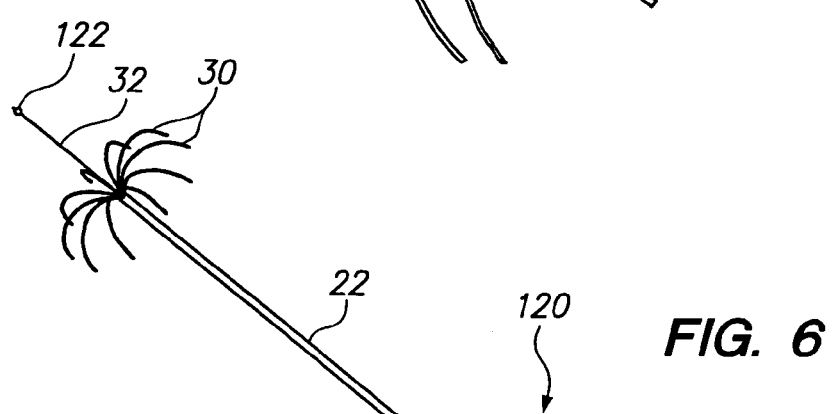
FIG. 6 is a complete perspective view of the RF ablation probe of FIG. 5.
Figure 6:
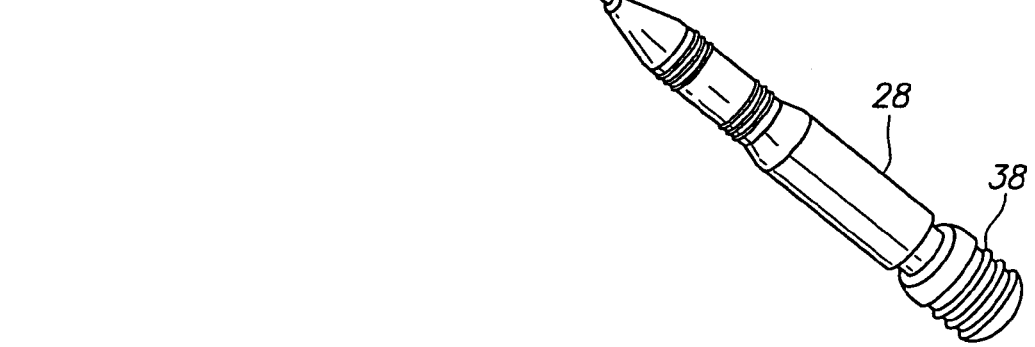

FIGS. 4-6 illustrate a radio frequency (RF) ablation probe 120 constructed in accordance with a preferred embodiment of the invention. The ablation probe 120 is similar to the LeVeen Needle™ electrode 20 previously described in the background section of this specification, and to the extent that the elements of these probes are similar, identical reference numbers have been used. As previously mentioned, the deployment member 32 is longitudinally movable within the inner cannula lumen 24 from a delivery position, in which the electrode tines 30 are positioned within the cannula lumen 24 (FIG. 4), to a deployed position, in which the electrode tines 30 extend distally out of the distal cannula opening 40 (FIGS. 5 and 6). The ablation probe 120 differs from the ablation probe 20 in that it has a tissue-penetrating member that substantially seals the distal cannula opening 40.

Figure 7:
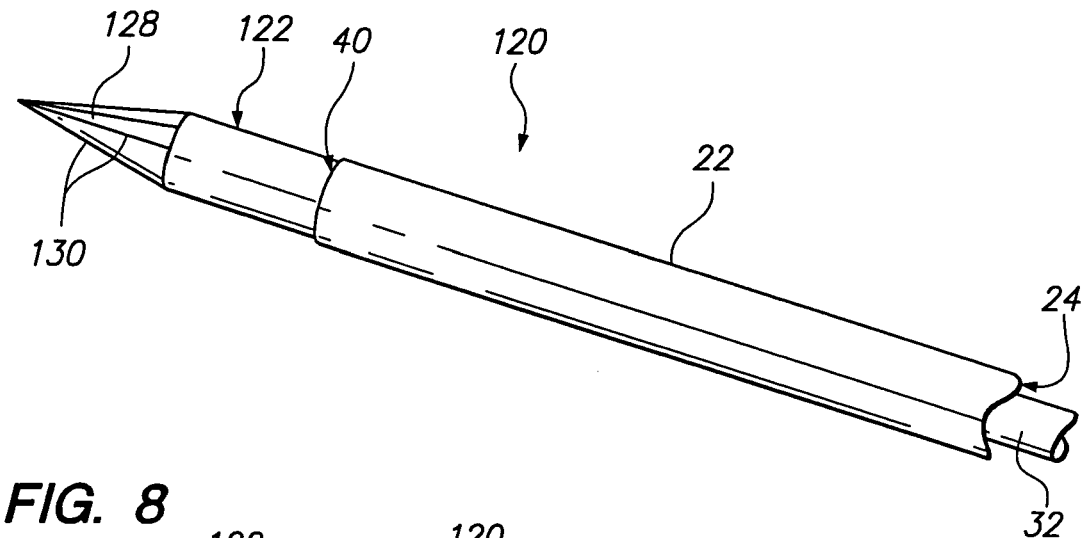
FIG. 7 is a partially cut-away perspective view of the distal end of the RF ablation probe of FIG. 4, particularly showing an alternative sealing member.

In particular, the ablation probe 120 comprises a tissue-penetrating sealing member 122 mounted to the distal tip of the tubular deployment member 32 at a location distal to the electrode tines 30. The sealing member 122 is composed of a suitably biocompatible rigid material, such as a biocompatible polymer or stainless steel. The sealing member 122 has a shape that allows it to substantially seal the distal cannula opening 40 and penetrate through solid tissue when the deployment member 32 is in the delivery position. As shown in FIG. 4, the sealing member 122 comprises a cylindrically-shaped base 124 that conforms to, and fits within, the circular distal cannula opening 40, and a conically-shaped distal tip 126 that extends out from the distal opening 40. Alternatively, as shown in FIG. 7, the sealing member 122 comprises a pyramidally-shaped distal tip 128. In this case, the resulting edges 130 form a faceted surface that facilitates ultrasonic visualization of the distal end of the ablation probe 120.

Figure 1:
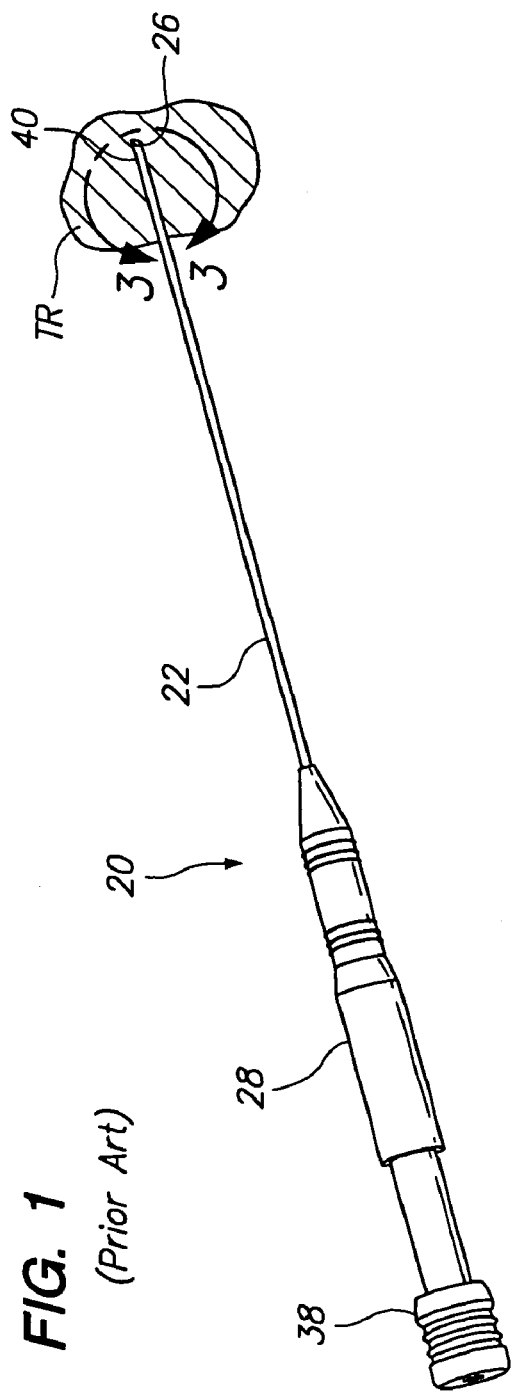
FIG. 1 is perspective view of a prior art radio frequency (RF) ablation probe.
Figure 2:
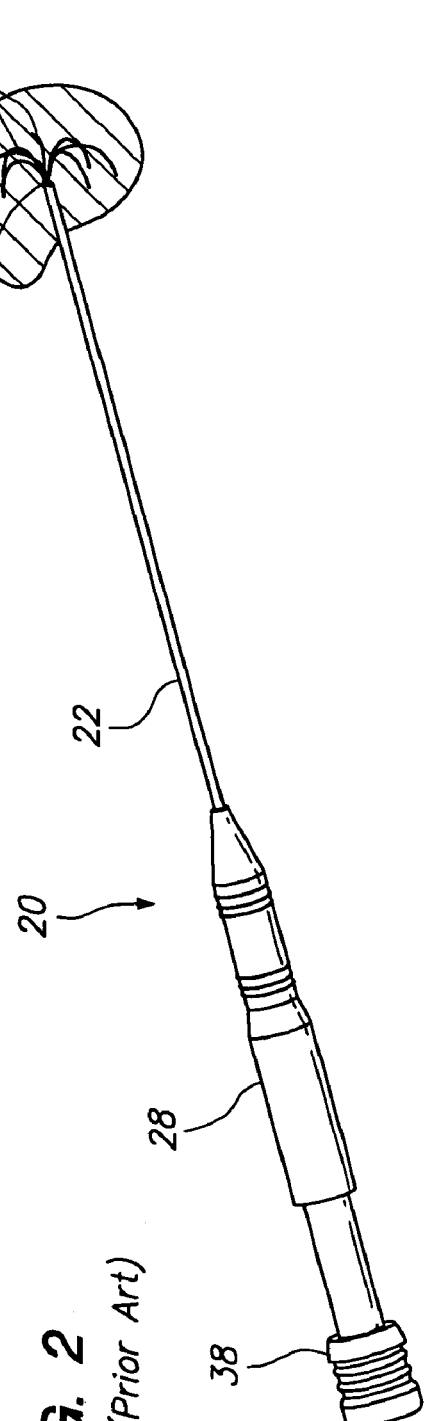
FIG. 2 is a perspective view of the RF ablation probe of FIG. 1, particularly showing an array of electrode tines deployed therefrom.
Figure 3:
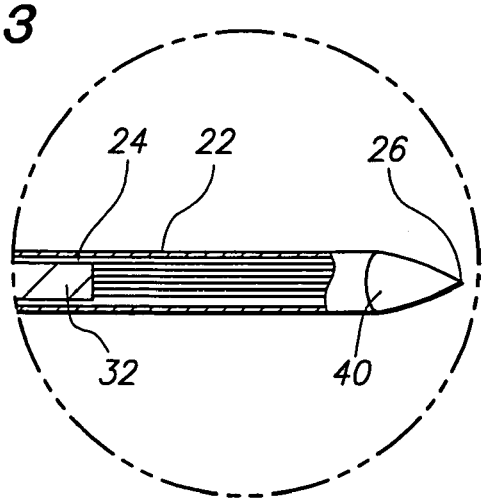
FIG. 3 is a magnified partially cutway view of the distal end of the RF ablation probe of FIG. 1, taken along the line 3-3.
Figure 8:
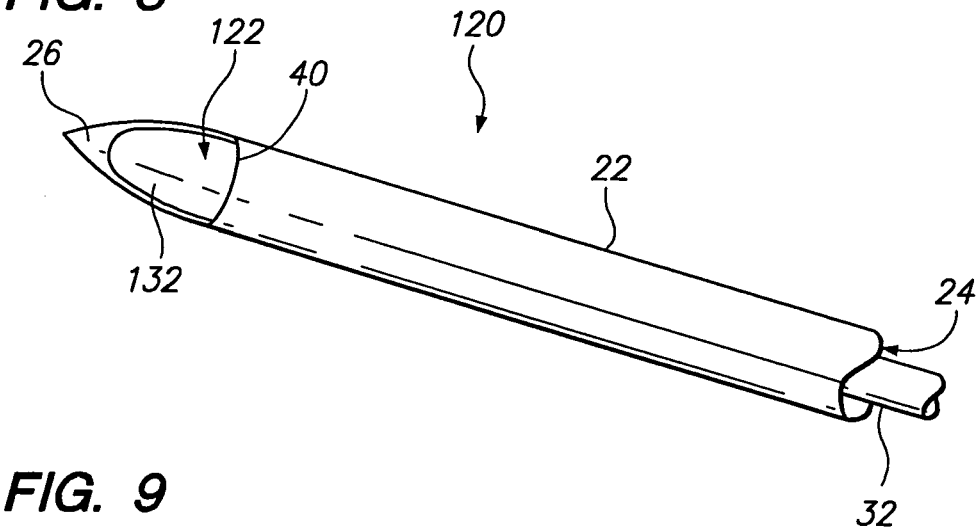
FIG. 8 is a partially cut-away perspective view of the distal end of the RF ablation probe of FIG. 4, particularly showing an alternative sealing member and cannula distal tip.
Figure 9:
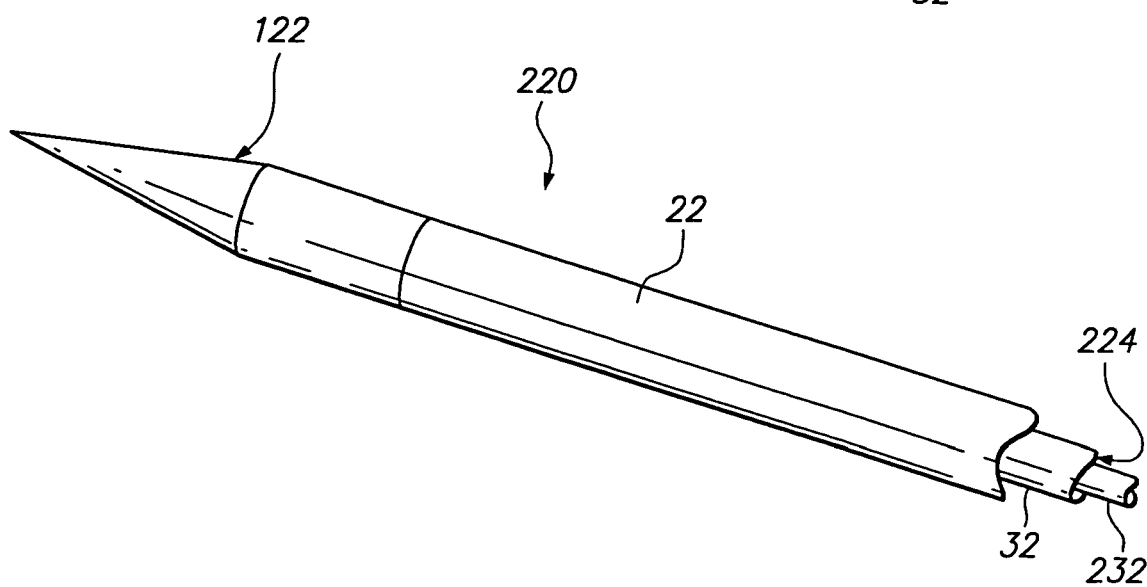
FIG. 9 is a partially cut-away perspective view of the distal end of another RF ablation probe constructed in accordance with a preferred embodiment of the invention.

It can be appreciated that, because the sealing member 122 is shaped to penetrate through tissue, the cannula 22 need not have a sharpened distal tip 26 (as illustrated in FIG. 3), but instead can have a blunted distal tip (as illustrated in FIGS. 4 and 7). Alternatively, as illustrated in FIG. 8, the sealing member 122 can have a blunted-tip 132, in which case, the cannula 22 comprises a sharpened distal tip 26 to facilitate introduction of the cannula 22 through the solid tissue.

The sealing member 122 may optionally have one or more functions in addition to providing the ablation probe 120 with a sealing and tissue-penetrating capability. For example, the sealing member 122 may function as an electrode, in which case, it can be composed of an electrically conductive material. Or the sealing member 122 may have temperature sensing functionality, in which case, a temperature sensor (not shown) can be mounted thereon. Or the sealing member 122 may have a fluid delivery opening (not shown) in fluid communication a fluid delivery lumen (not shown) longitudinally extending through the deployment member 32.

As illustrated in FIG. 5, the sealing member 122 distally extends beyond the distal cannula opening 40 when the deployment member 32 is in the deployed position, thereby allowing the electrode tines 30 to be extended therefrom without obstruction from the sealing member 122. As can be appreciated, the sealing member 122 will extend from the distal cannula opening 40 a fixed distance at least equal to the length of the electrode tines 30 when fully deployed.

FIGS. 9-12 illustrate another RF ablation probe 220 constructed in accordance with a preferred embodiment of the invention. The ablation probe 220 is similar to the previously described ablation probe 120, with the exception that the sealing member 122 is independently deployable from the electrode tines 30. In particular, the ablation probe 220 comprises an inner deployment member 232 seated coaxially within a lumen 224 extending through the first or outer deployment member 32. The ablation probe 220 comprises another proximal plunger 238 (shown in FIG. 12) fixed to the inner deployment member 232, such that movement of the plunger 238 relative to the handle 28 provides for alternate deployment of the sealing member 122 out of, or into, the distal cannula opening 40.

Figure 10:
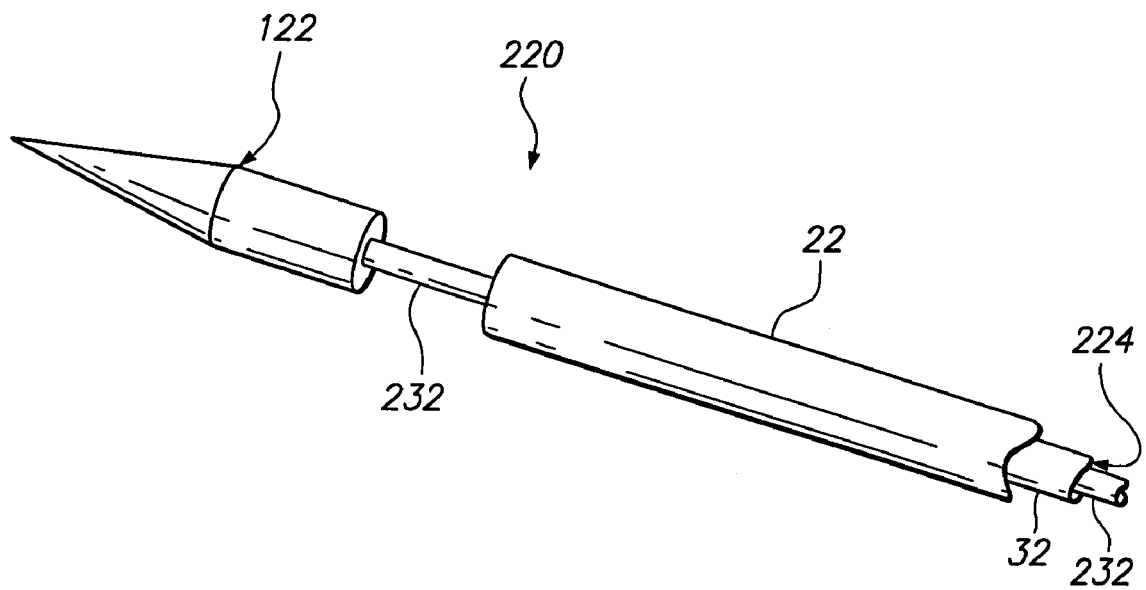
FIG. 10 is a partially cut-away perspective view of the distal end of the RF ablation probe of FIG. 9, particularly showing deployment of the sealing member.
Figure 11:
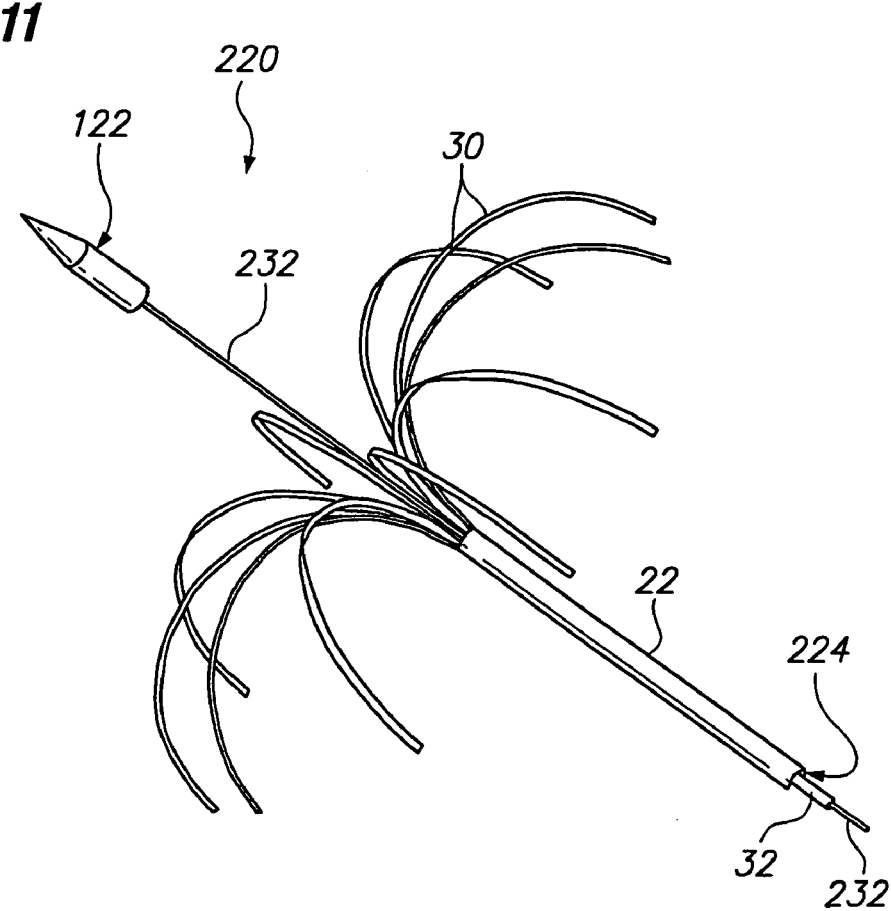
FIG. 11 is a partially cut-away perspective view of the distal end of the RF ablation probe of FIG. 9, particularly showing deployment of the electrode tine array.
Figure 12:
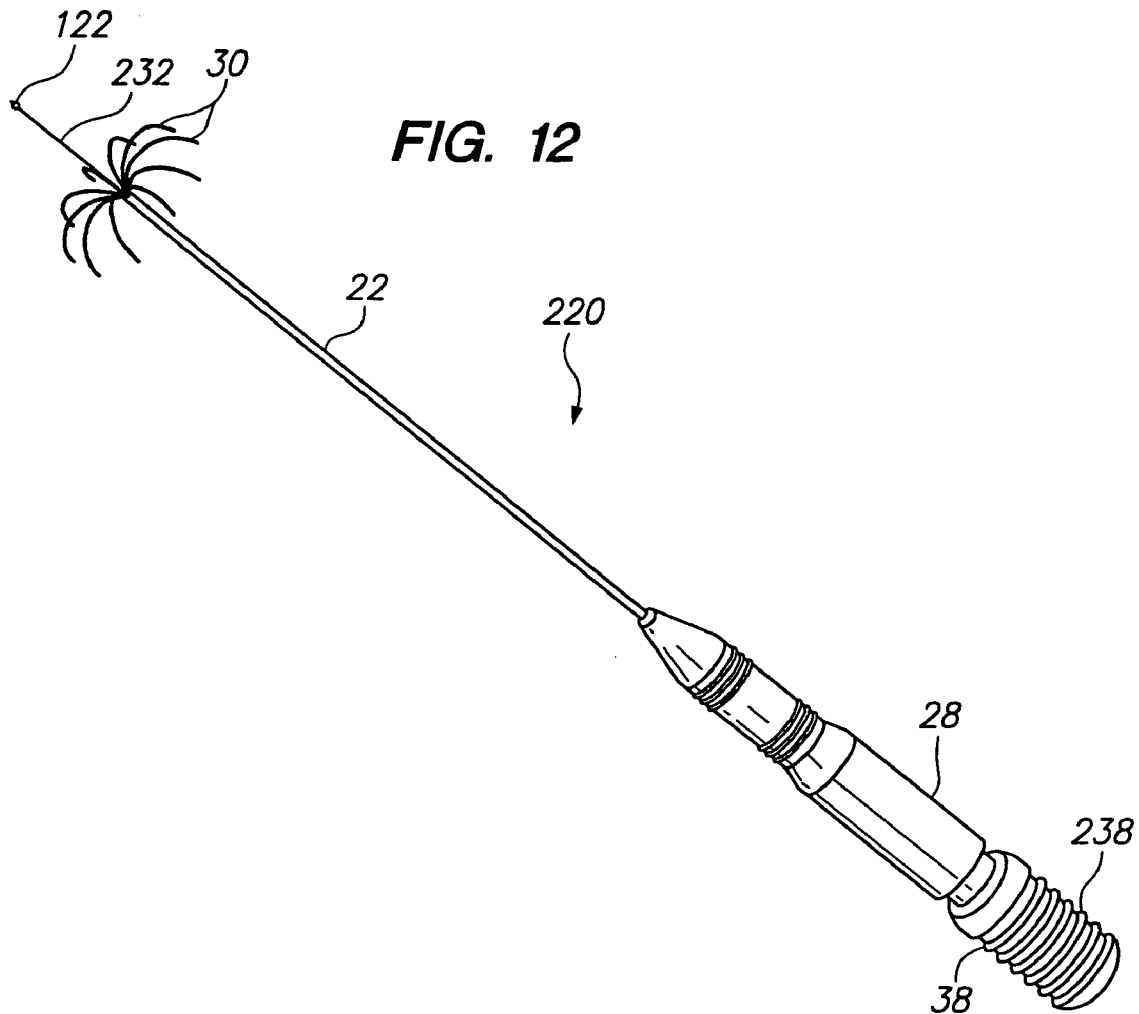
FIG. 12 is a complete perspective view of the RF ablation probe of FIG. 11.

Thus, the deployment member 232 is movable from a delivery position, in which the sealing member 122 substantially seals the distal cannula opening 40 (FIG. 9), to a deployed position, in which the sealing member 122 extends distally out of the cannula distal opening 40 (FIG. 10). As can be appreciated, the distance that the sealing member 122 is deployed from the distal cannula opening 40 can be varied independently of the electrode tines 30 by moving the plungers 38 and 238 relative to each other. Preferably, the sealing member 122 is deployed from the cannula distal opening 40 the minimal distance required to provide spatial clearance for deployment of the electrode tines 30 (FIG. 11). In this manner, tissue trauma otherwise caused by inserting the sealing member 122 through tissue distal to the treatment region is minimized.

Figure 13:
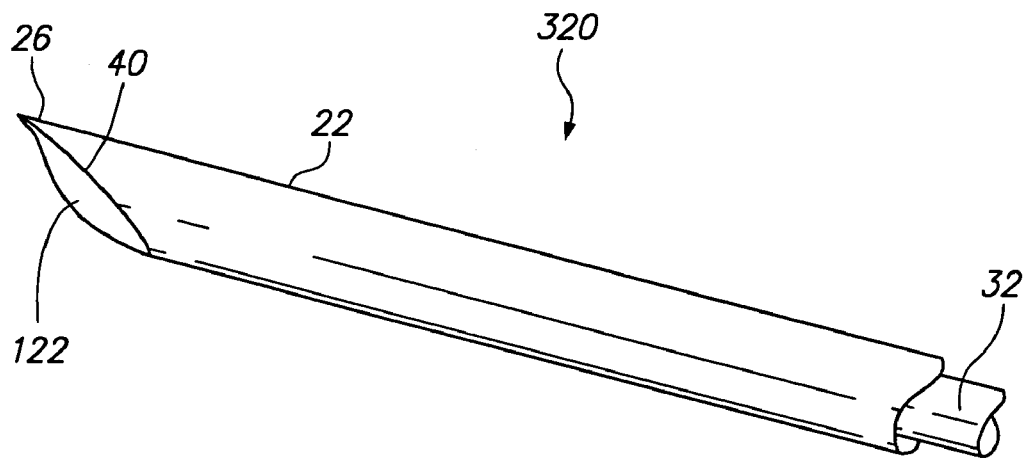
FIG. 13 is a partially cut-away perspective view of the distal end of still another RF ablation probe constructed in accordance with a preferred embodiment of the invention.
Figure 14:
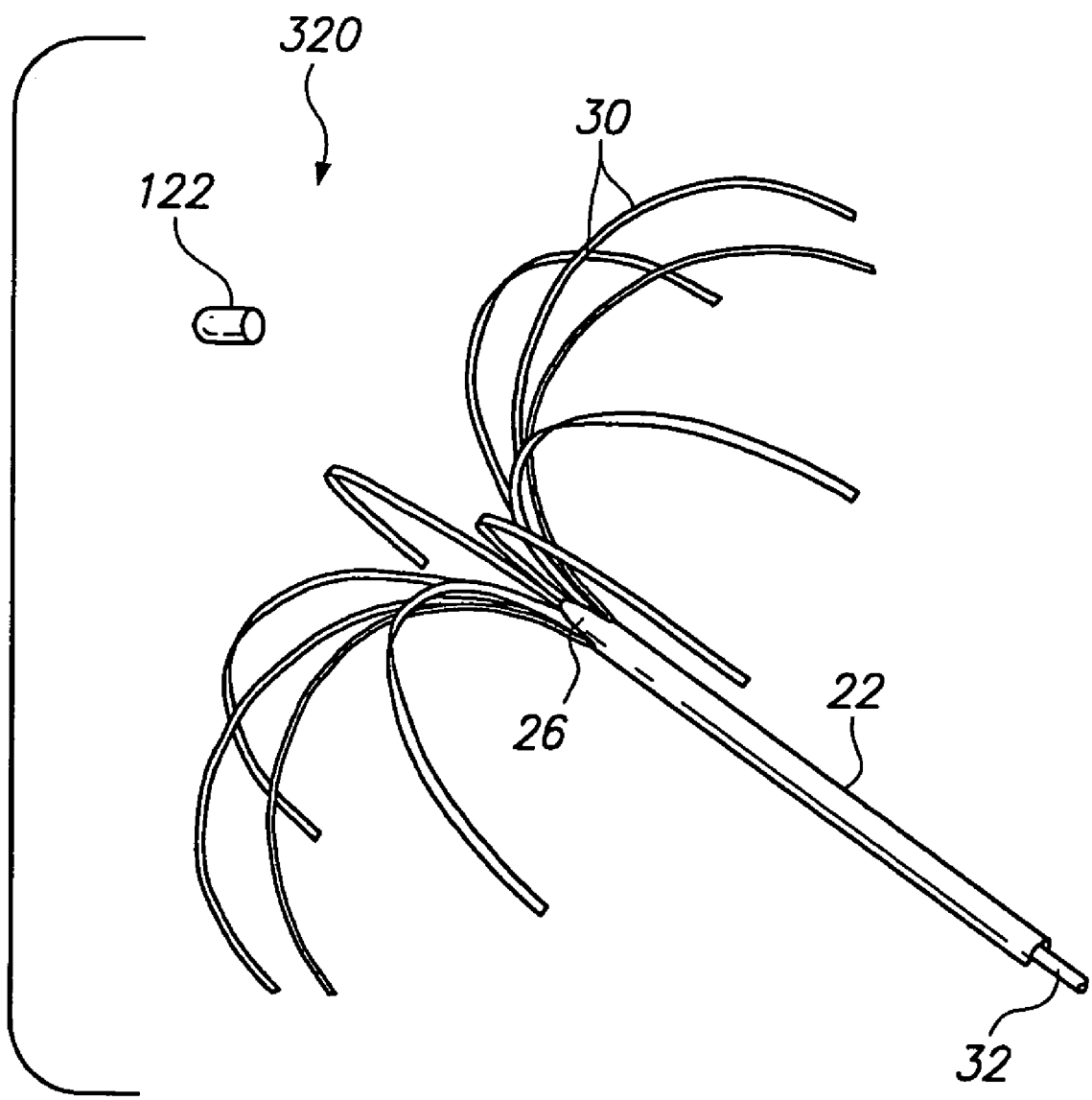
FIG. 14 is a partially cut-away perspective view of the distal end of the RF ablation probe of FIG. 13, particularly showing deployment of the sealing member and electrode tine array.

FIGS. 13 and 14 illustrate still another RF ablation probe 320 constructed in accordance with a preferred embodiment of the invention. The ablation probe 320 is similar to the previously described ablation probe 120, with the exception that the sealing member 122 is not carried or mounted to the distal end of the deployment member 32. Instead, the sealing member 122 is frictionally fit within the distal cannula opening 40, such that movement of the deployment member 32 from the delivery position (FIG. 13) to the deployed position (FIG. 14) detaches the sealing member 122 from the cannula 22, thereby allowing the electrode tines 30 to be deployed from the distal cannula opening 40. In this case, the sealing member 122 is preferably composed of a bioabsorbable material. In the illustrated embodiment, the sealing member 122 is composed of soft, quickly dissolvable bioabsorbable material, such as bone wax. In this case, the cannula 22 preferable has a sharpened, tissue-penetrating distal tip 26, as illustrated in FIGS. 13 and 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed:

1. A medical device for the delivery of energy to body tissue, comprising:
   an elongate delivery cannula having a lumen in communication with a distal opening;
   a deployment member longitudinally movable in the lumen;
   an array of electrode elements secured to a distal end of the deployment member, the deployment member movable from a delivery position, in which the electrode elements are positioned within the lumen, to a deployed position, in which the electrode elements extend distally out of the cannula distal opening; and
   a sealing member comprising a tissue-penetrating distal tip and fixedly carried on a distal end of the deployment member and distal to the electrode elements, the sealing member at least partially extending from, and substantially sealing, the distal cannula opening when the deployment member is in the delivery position, wherein movement of the deployment member to the deployed position moves the sealing member distal to the distal cannula opening, thereby allowing the electrode elements to be extended therefrom without obstruction from the sealing member, wherein the sealing member comprises one or more of an electrode and a temperature sensor,
   wherein, when the deployment member is in the deployed position, distal ends of the electrode elements evert away from the sealing member.

2. The device of claim 1, wherein the sealing member has a conically-shaped distal tip.

3. The device of claim 1, wherein the sealing member has a pyramidally-shaped distal tip.

4. The device of claim 1, wherein the cannula has a blunted distal tip.

5. The device of claim 1, wherein the electrode elements are electrode tines.

6. The device of claim 5, wherein the electrode tines are substantially linear when constrained in the cannula lumen and are curved when deployed outside of the cannula lumen.

7. The device of claim 1, wherein the sealing member is configured for preventing coring of solid tissue.

8. A medical device for the delivery of energy to body tissue, comprising:
   an elongate delivery cannula having a lumen in communication with a distal opening;
   a first deployment member longitudinally movable in the lumen, the first deployment member having a lumen therein;
   an array of electrode elements secured to a distal end of the first deployment member, the first deployment member movable from a delivery position, in which the electrode elements are positioned within the cannula lumen, to a deployed position, in which the electrode elements extend distally out of the cannula distal opening and evert;
   a second deployment member longitudinally movable in the lumen of the first deployment member; and
   a sealing member comprising a tissue-penetrating distal tip and fixedly carried on a distal end of the second deployment member, the sealing member comprising one or more of an electrode and a temperature sensor, the second deployment member being movable from a delivery position, in which the sealing member is positioned proximate to and substantially sealing the cannula distal opening, to a deployed position, in which the sealing member is extended distally from the cannula distal opening, wherein the first and second deployment members are moveable independent of one another, wherein, when the first deployment member is in the deployed position, distal ends of the electrode elements evert away from the sealing member.

9. The device of claim 8, wherein the sealing member has a conically-shaped distal tip.

10. The device of claim 8, wherein the sealing member has a pyramidally-shaped distal tip.

11. The device of claim 8, wherein the cannula has a blunted distal tip.

12. The device of claim 8, wherein the electrode elements are electrode tines.

13. The device of claim 12, wherein the electrode tines are substantially linear when constrained in the cannula lumen and are curved when deployed outside of the cannula lumen.

14. The device of claim 8, wherein the sealing member is configured for preventing coring of solid tissue.

15. A medical device for the delivery of ablation energy to body tissue, comprising:
    an elongate delivery cannula having a lumen in communication with a distal opening;
    a deployment member longitudinally movable in the lumen;
    at least one ablation element secured to a distal end of the deployment member, the deployment member movable from a delivery position, in which the at least one ablation element is positioned within the lumen, to a deployed position, in which the at least one ablation element extends distally out of the cannula distal opening; and
    a sealing member comprising a tissue-penetrating distal tip and carried on a distal end of the deployment member, the sealing member comprising one or more of an electrode and a temperature sensor, the sealing member at least partially extending from, and substantially sealing, the distal cannula opening when the deployment member is in the delivery position, wherein movement of the deployment member to the deployed position moves the sealing member distal to the distal cannula opening a fixed distance at least equal to the length of the at least one ablation element when fully deployed,
    wherein, when the deployment member is in the deployed position, a distal end of the at least one ablation element everts away from the sealing member.

16. The device of claim 15, wherein the sealing member has a conically-shaped distal tip.

17. The device of claim 15, wherein the sealing member has a pyramidally-shaped distal tip.

18. The device of claim 15, wherein the cannula has a blunted distal tip.

19. The device of claim 15, further comprising another deployment member longitudinally movable in the lumen, wherein the sealing member is carried on a distal end of the other deployment member.

20. The device of claim 19, wherein the other deployment member is positioned coaxially with the deployment member.

21. The device of claim 20, wherein the other deployment member is positioned telescopically with the deployment member.

22. The device of claim 20, wherein the other deployment member and the deployment member are movable independent of one another.

23. The device of claim 15, wherein the at least one ablation element is at least one electrode tine.

24. The device of claim 23, wherein the at least one electrode tine is substantially linear when constrained in the cannula lumen and is curved when deployed outside of the cannula lumen.

25. The device of claim 15, wherein the sealing member is configured for preventing coring of solid tissue.

* * * * *

UNITED STATES PATENT AND TRADEMARK OFFICE
CERTIFICATE OF CORRECTION

PATENT NO. : 8,142,427 B2
APPLICATION NO. : 10/831244
DATED : March 27, 2012
INVENTOR(S) : Pearson et al.

Page 1 of 1

It is certified that error appears in the above-identified patent and that said Letters Patent is hereby corrected as shown below:

In the Claims:

Col. 8, claim 15, line 7, remove "fixed"

Col. 8, claim 22, line 28, replace "The device of claim 20, wherein the other deployment" with -- The device of claim 19, wherein the other deployment --

Signed and Sealed this
Twenty-fourth Day of July, 2012

David J. Kappos
*Director of the United States Patent and Trademark Office*